United States Patent [19]

Diamond

[11] 4,232,582

[45] Nov. 11, 1980

[54] ACOUSTICAL STRINGED MUSICAL INSTRUMENT PICK-UP

[76] Inventor: Marc Diamond, Wildcat Hill Rd., Harwinton, Conn. 06791

[21] Appl. No.: 26,873

[22] Filed: Apr. 4, 1979

[51] Int. Cl.[3] .......................... G10D 1/08; A61B 7/02

[52] U.S. Cl. .......................................... 84/267; 84/465; 84/470 R; 181/131

[58] Field of Search ............ 84/1.16, 267, 465, 470 R; 181/131, 141

[56] References Cited

U.S. PATENT DOCUMENTS

| | | | |
|---|---|---|---|
| 2,230,794 | 2/1941 | Danischewsky | 181/131 |
| 2,505,124 | 4/1950 | Lepeschkin | 181/131 |
| 3,830,334 | 8/1974 | Costa | 181/131 |
| 4,112,809 | 9/1978 | Sjostrand et al. | 84/1.16 |
| 4,135,426 | 1/1979 | Rickard | 84/1.16 |

*Primary Examiner*—J. V. Truhe
*Assistant Examiner*—Forester W. Isen
*Attorney, Agent, or Firm*—Stempler and Munves

[57] ABSTRACT

An apparatus for transmitting acoustical energy from a stringed musical instrument having a bridge and string anchor to a listener comprising an energy pick-up chamber, an energy transmission member and a means for transmitting said energy to a listener is disclosed. The pick-up chamber is located at said bridge and is in resonant contact with the strings. It has at least one opening through which an elongated, hollow, energy transmission member is connected to the interior of the chamber. The means is mounted on the other end of the hollow member for transmitting the musical energy to the ears of a listener.

23 Claims, 8 Drawing Figures

FIG. 3
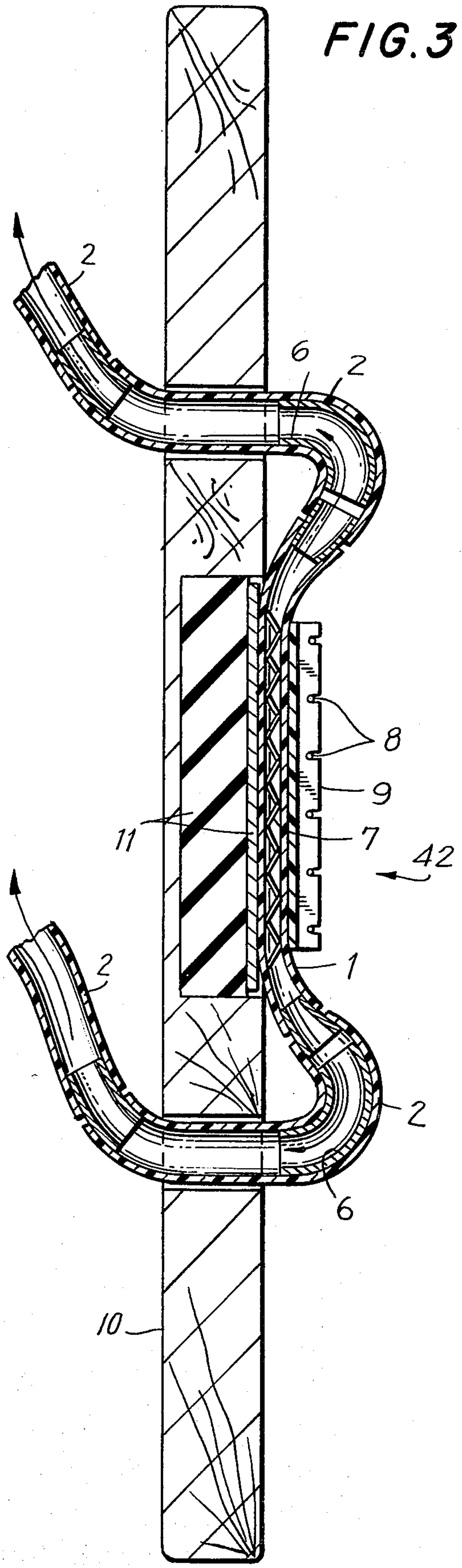
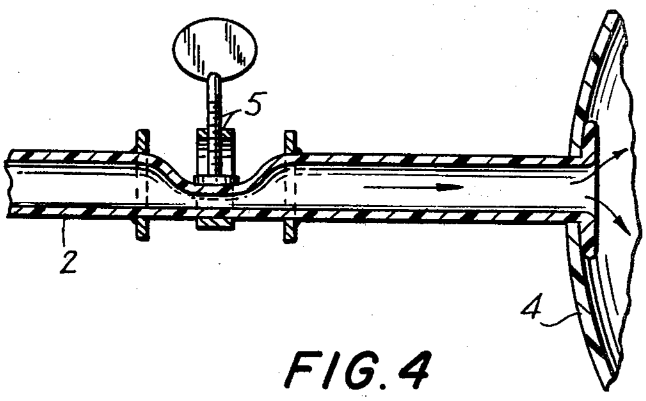
FIG. 4

FIG. 7
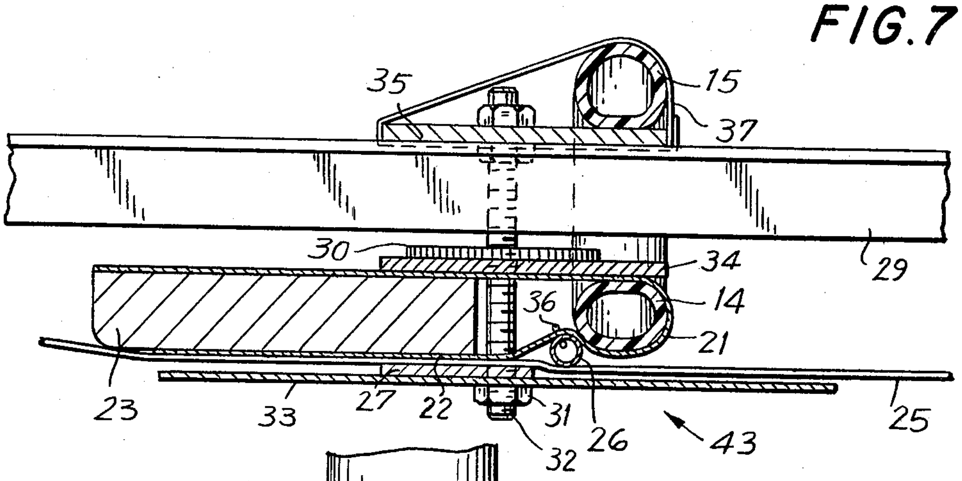
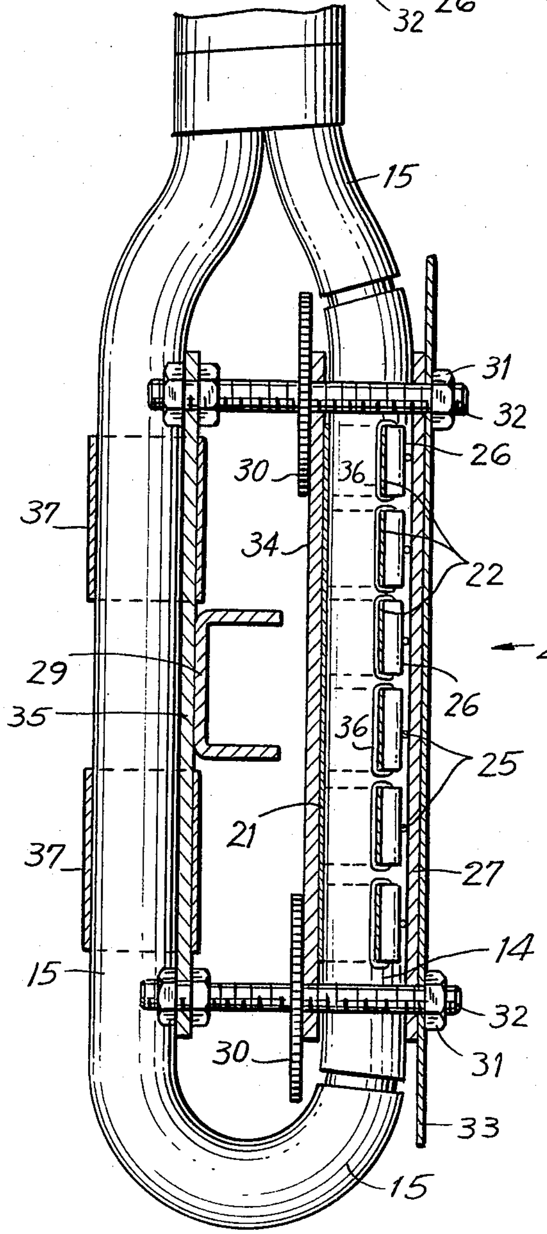
FIG. 8

ACOUSTICAL STRINGED MUSICAL INSTRUMENT PICK-UP

BACKGROUND OF THE INVENTION

This invention is an apparatus for feeding the output of a stringed musical instrument back to a person, usually the player. The apparatus is inexpensive to make and easy to use. It will revolutionize stringed musical instrument instruction by permitting a teacher to give more individualized instruction to each member of a student group. Each student will be able to learn at a rate commensurate with his innate ability, something heretofore available only through expensive private instruction or with the use of expensive and complex electronic equipment.

It is a common situation in schools at all levels to observe large groups of students gathered in one room to study music. When teaching groups of students to play a particular stringed instrument, it has previously been the practice to have the entire class play the same notes in unison or to have each member demonstrate his ability by playing alone while the rest of the group await their turn. This has been necessary to avoid the distraction and loss of concentration a student would experience were all students to play simultaneously at different pitches and tempos.

The traditional teaching methods using standard instruments force all to be taught at a uniform rate that is roughly commensurate with the ability of the average learner in the group.

This is because the workspace of music is usually confined to one large music room. However, each individual has a different aptitude for musical instruction. Moreover, each student learns at a varying rate of speed.

The present invention is directed toward this pedagogical problem. It isolates each student sufficiently for him to play his instrument simultaneously with the other students without the distraction that would normally be caused by the interference of the sound of the different instruments. It also allows each student to hear his own instrument at ordinary concert levels. Consequently, the students need not play at the same rate or even the same music. Moreover, the instructor can work with each individual in the group while the others are practicing thus giving the equivalent of individual instruction.

The most ideal teaching conditions occur when the apparatus is used in connection with a musical instrument whose sound output is capable of being damped without affecting its playing characteristics. There are a wide variety of possibilities in quieting stringed instruments. For example, guitar may be taught using a solid-body instrument having no resonating chamber like an electric guitar without its associated electronic equipment; or, the guitar body may simply comprise a solid piece of wood. Electric guitars are widely played without amplification during practice. The pitch of the notes is unaffected by this arrangement.

Moreover, guitars need not have a solid body. I have found that an open frame outlining the shape of the solid body and supporting its strings can be substituted for the solid body thereby eliminating vibrations within the solid body. This embodiment can be externally quieter than the solid-body version. However, like the solid-body instrument, the general playing characteristics remain unchanged. The open-frame design is applicable to all stringed instruments.

A similar effect could be obtained with an acoustical guitar by stuffing its resonating chamber with a soft, sound-absorbent material to dampen the sound output. This is clumsier. Obviously, this also can be done with any stringed instrument that uses a resonating chamber to amplify the sound of the strings.

Using the apparatus of this invention, the students learning on damped instruments can be seated closer together without being disturbed by neighboring instruments than students learning on undamped instruments while still hearing the music at normal output levels. This means that more students can be taught in a given music room. It is also easier on the instructor's ears and nerves if the instruments are damped. Use of the apparatus in connection with damped instruments is also ideal for a student who is practicing at home. It allows him to play the instrument without annoying other members of the household or neighbors.

GENERAL DESCRIPTION OF THE INVENTION

The invention is an apparatus for transmitting acoustical energy (namely, music) from a stringed instrument, having a bridge, to a listener. The listener is usually the individual playing the instrument. For the purposes of example only, the invention is described herein in solid-body and open-frame guitar embodiments. However, it will be understood from the description that the invention may be used with many other types of stringed instruments including the violin, banjo, mandolin, bass, viola, cello, and piano. Embodiments in which the instrument's acoustical output is externally damped are preferred.

The apparatus comprises an energy pick-up chamber with at least one opening located at the bridge of the instrument and in resonant contact therewith, an energy transmission member, and means for transmitting the musical energy to the listener's ears.

For guitars, a pick-up chamber of five-sixteenths of an inch in diameter has been found to be a desirable size. Larger chambers can be substituted. This results in greater output. Smaller chambers are also possible and they result in lower output.

It is preferred that the hollow energy transmission member comprise a flexible tube. It is most preferred that the pick-up chamber have two openings with a flexible tube connected to the interior of said chamber through each of said openings.

In this embodiment, it is also preferred that the listening means be a headset means comprising a pair of padded, concave earpieces surrounding each ear. Each earpiece has an opening therein and the interior of each said earpiece is connected to one of the flexible tubes through the opening. In this embodiment, each earpiece forms a small chamber about each ear of the listener. Only small amounts of acoustical energy are required to stimulate the air in this chamber in order to create sound at normal listening levels.

It is most preferred that air flow control means be located in the pick-up chamber, hollow energy transmission member, or listening means or in any combination thereof to control the amount of acoustical energy being transmitted to the listener.

Where the energy transmission member comprises a flexible tube, the air flow control means may comprise adjustable compression means mounted on said energy transmission member for selectively changing the cross-sectional area of said member.

The air flow control means may also comprise openings downstream of the pick-up chamber in the energy transmission member or the listening means, or both, and means for selectively closing said openings.

It is preferred that the tube support means such as a rigid plastic or metal tube formed in the proper shape be provided in tube sections subject to constant bending to prevent collapse of said flexible tube.

It is preferred that the energy pick-up chamber be composed of a flexible material. Flexible rubbery or plastic materials are recommended. It is most preferred that the pick-up chamber be tubular in shape. A string support should be in resonant contact with said chamber.

When the pick-up chamber is flexible, it is also preferred to have a chamber support to prevent the closing of the pick-up chamber from the pressure exerted by the strings. The chamber support can be located inside or outside the bridge. The chamber support can comprise a semi-rigid C-shaped member encompassing said pick-up chamber on three sides and an anti-collapse member adjacent the fourth side of said pick-up chamber in the mouth of said C-shaped member to prevent said C-shaped member from being collapsed by pressure exerted by said strings upon said chamber. The C-shaped member can be a thin, tin-plated steel plate bent into the proper shape. The anti-collapse member is located between the resonating chamber and strings anchor located at the bridge end of the guitar. The plate adds support to the chamber support and helps to control vibration of the C-shaped member.

Alternatively, the chamber support can comprise means inside said chamber such as a spring to prevent the collapse of said chamber due to string pressure or support means between the chamber and string anchor under the strings to alleviate string pressure on the chamber. Any of the chamber support means may be used alone or in combination with other such support means.

It is preferred that at least the string support be mounted on said C-shaped member above the pick-up chamber to support the strings.

In a stringed instrument having a plurality of strings, it is most preferred that each string be supported by a separate string support; that each support be adjacent at least one other support, and that each string support be mounted on a separate finger of said C-shaped member such that each support is substantially resonantly isolated from each adjacent support. A wider finger will result in greater acoustical output to the earpiece.

It is also preferred that the string supports be tubular; that each string support be tied to its corresponding finger by durable string; and that a clamping plate be located over each of said strings between each said string support and said string anchor to force each said string against each string support and promote resonant contact therebetween and control excess vibration. The tubular string supports may be made of surgical steel.

It is preferred that the instrument have a non-resonant body. A solid body is preferred and an open-frame body is most preferred. The solid body can be made of any suitable material such as plastic or wood. The open-frame body can be made of any material with sufficient rigidity to maintain its shape against the pull of the strings. An aluminum frame with a steel backbone has been found to be suitable.

On a solid-body instrument, the bridge can further comprise a damping material mounted on the instrument body below the pick-up chamber for minimizing the flow of acoustical energy from the strings through the bridge to the body. This provides additional damping of external output. Open-frame instruments generate less resonant acoustical energy and usually do not need such damping.

It is preferred that the bridge be mounted on adjusting means to permit moving the strings a selected distance from the body of the instrument. The strings can therefore be adjusted to the proper height above the fret board.

It is also preferred that a protective plate be mounted above said bridge to cover it. This is most preferred for bowed and plucked instruments to prevent the bridge from being jarred or misaligned by the player's hand.

The degree of hardness of the energy pick-up chamber, chamber support, string support, and damping material will affect the timbre of the instrument. Harder materials cause a steel string effect while softer materials result in a softer, nylon string guitar effect. The timbre of the instrument can be made to sound as desired by the proper selection of the combination of materials used to construct the bridge.

Internal resonance is affected by the positioning of the C-shaped member, string support, and anti-collapse member in relation to the pick-up chamber. For example, if the anti-collapse member is moved slightly back from the chamber toward the strings anchor, then resonance, or decay time, is increased.

The foregoing and other objects and advantages of the invention, as well as the basic characteristics thereof, including equivalents and substitutions therefor, are better understood by giving consideration to the detailed description of the various embodiments of the invention.

In the accompanying drawings, in which like reference characters indicate like parts, FIG. 1 is a perspective view showing a solid-body guitar embodiment of the invention;

FIG. 3 is a partial cross-sectional view along lines 3—3 of FIG. 1;

FIG. 4 is a partial cross-sectional view along lines 4—4 of FIG. 1;

FIG. 7 is a partial cross-sectional view along lines 7—7 of FIG. 5; and FIG. 8 is a partial cross-sectional view along lines 8—8 in FIG. 5.

Figure 2:
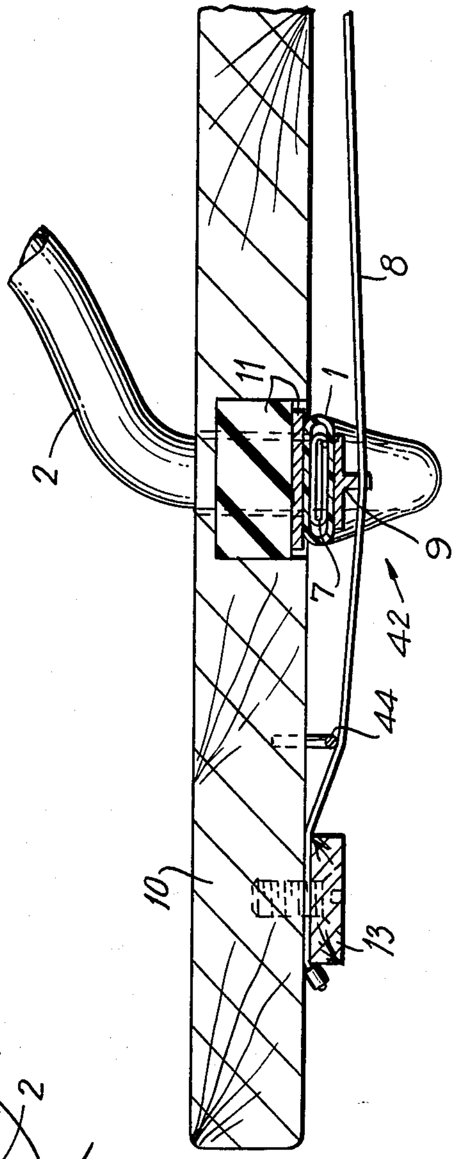
FIG. 2 is a partial cross-sectional view along lines 2—2 of FIG. 1.
Figure 1:
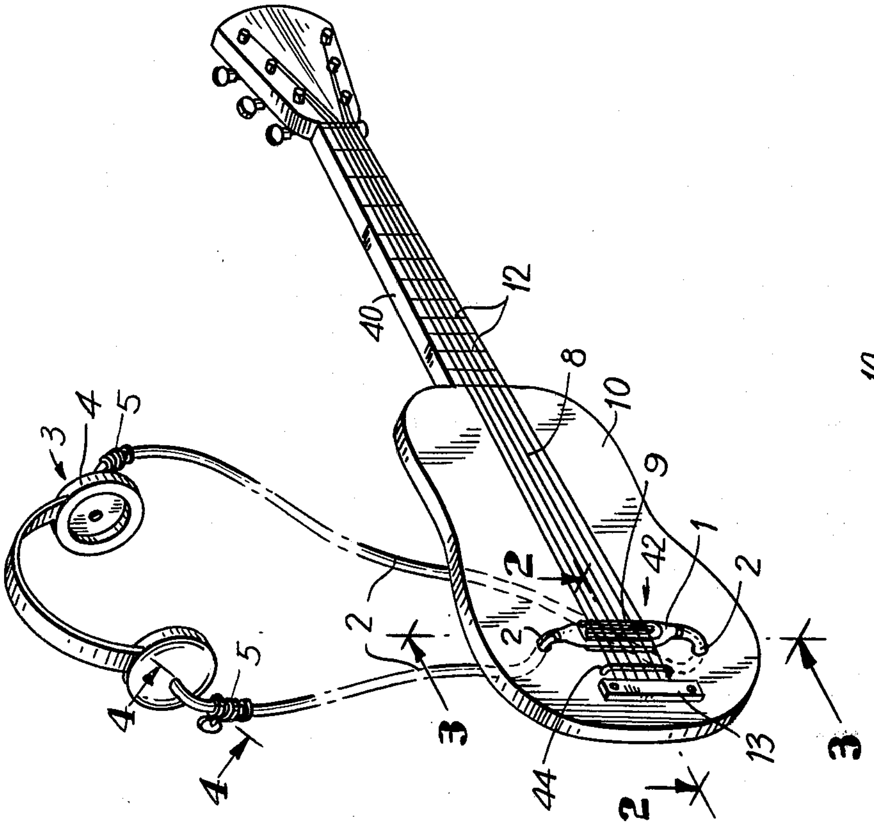

Referring to FIGS. 1-4, the apparatus comprises a guitar having a solid body 10, neck 40, frets 12, strings 8 and string anchor 13. In place of an ordinary guitar bridge, bridge 42 is substituted.

Bridge 42 comprises an energy pick-up chamber 1, string support 9, chamber support 7 and damping material 11. Pick-up chamber 1 is of a flexible plastic material and chamber support 7, which prevents complete collapse of the chamber, is a spring. Chamber support 44 also alleviates some of the string pressure on the chamber. The damping material 11 can comprise rubber or other vibration absorbent material.

The pick-up chamber 1 is tubular and connected at either end to an energy transmission member 2 which are simply hollow, flexible plastic tubes. Mounted on the other end of each tube 2 is headset 3 comprising earpieces 4.

Airflow control means 5 are mounted on each transmission tube 2. By means of a simple screw and ring combination, means 5 can be used to selectively compress each tube 2. By reducing the cross-sectional area of each said tube 2, the volume of the sound reaching each earpiece 4 is similarly reduced.

After the point where tube 2 is connected to chamber 1, it is subject to bending along certain portions of its length. Tube support means 6 (FIG. 3) is provided to keep tubes 2 open and to maintain a uniform cross-sectional area. Tube support 6 can comprise a rigid plastic or metal tube or even any other means such as a spring that will keep tubes 2 open.

Figure 5:
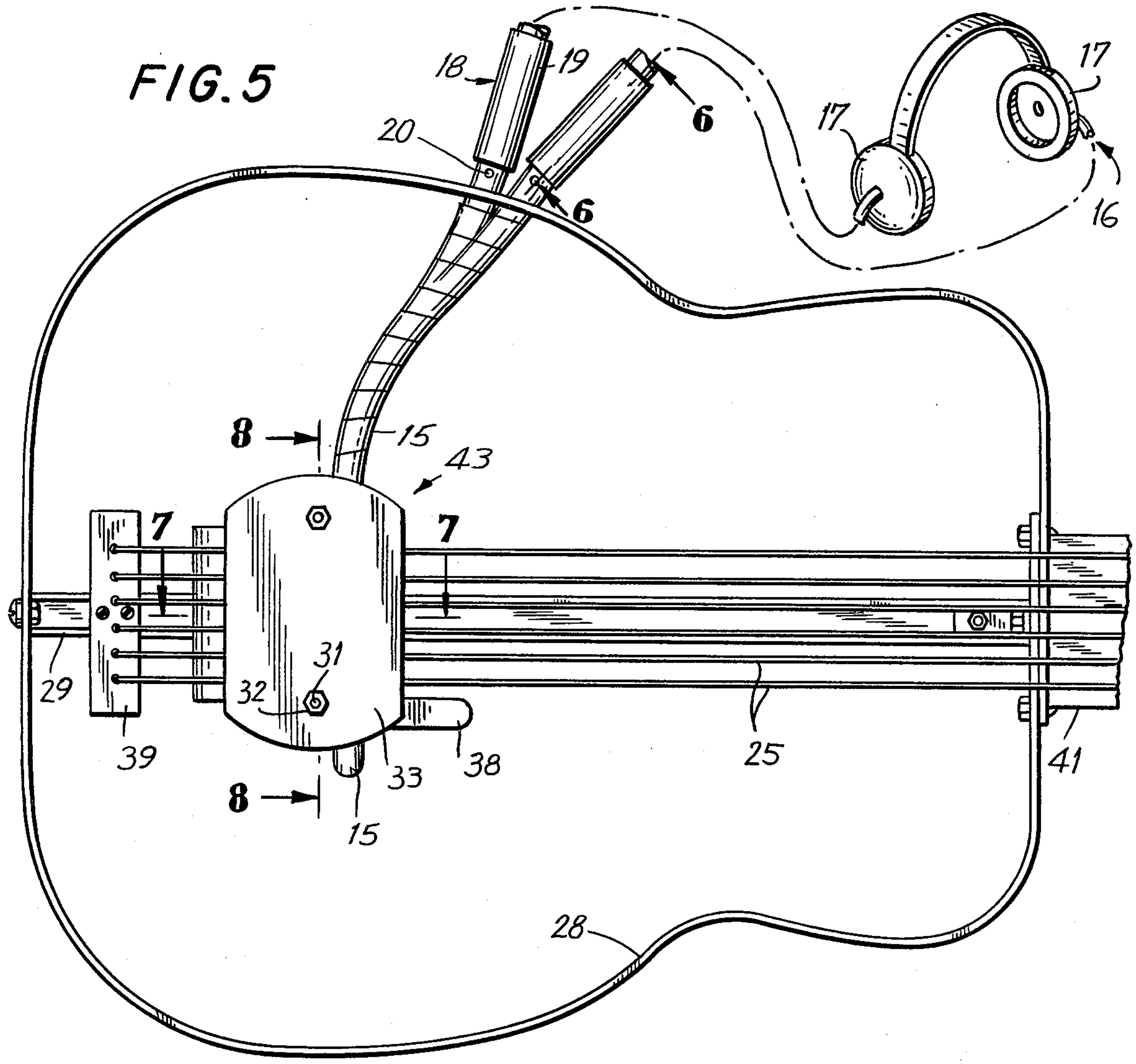
FIG. 5 is a plan view showing an open-frame guitar embodiment of the invention.
Figure 6:
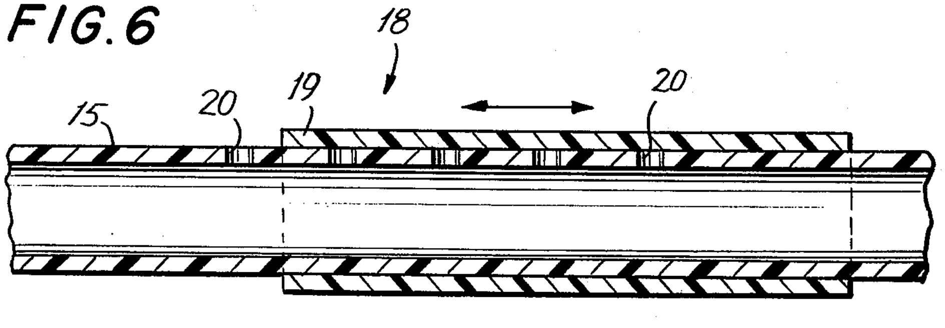
FIG. 6 is a partial cross-sectional view along lines 6—6 of FIG. 5.

Referring to FIGS. 5–8, an open-frame embodiment of the invention is shown. It comprises an aluminum open-frame 28 and steel backbone 29 upon which the remaining features are mounted. They comprise neck 41, strings 25, string anchor 39 and bridge 43.

The bridge comprises an energy pick-up chamber which is a flexible plastic tube 14. It is surrounded on three sides by support means comprising C-shaped member 21 and anti-collapse plate 23. C-shaped member 21 can be a thin tin-plated steel plate that has been bent into the proper shape. The anti-collapse plate 23 can be of any material that is sufficiently rigid to support the open end of the C-shaped member.

A separate surgical steel tubular string support 26 is tied by support string 36 between each string 25 and the C-shaped member. C-shaped member 21 has fingers 22 formed at one end such that each tubular string support 26 rests on a substantially resonantly isolated finger 22. The fingers 22 are most easily seen in FIG. 8 and the tubular supports 26 are visible due to the section taken therein.

Bridge plate 34 spans the two bridge support bolts 32 and may be adjusted along bolts 32 by wide bridge adjusting nuts 30 and nuts 31 so that the height of the bridge and strings above the neck 41 can be adjusted. Clamping plate 27 also spans between each bolt 32 and forces each string 25 against its respective tubular support 26 to promote resonant contact therebetween and to control excess vibration.

Protective plate 33 is provided above clamping plate 27 to protect the delicate bridge mechanism from being misaligned by an accidental brush of the player's hand.

Bolts 32 are affixed to open-frame 28 via base plate 35 which in turn is affixed to steel backbone 29.

The energy transmission member comprises a flexible tube 15 connected to pick-up chamber 14 at both ends. The tube 2 which passes behind the steel backbone is affixed to base plate 35 by fasteners 37 which can comprise tape or any other suitable means which will prevent tube 2 from shifting position. Finger rest 38 is provided at approximately the same level below the strings as the guitar body would be if it were a solid-body guitar for the convenience of the player.

Air flow control means 18 comprise openings 20 in each tube 15 and tubular slide 19 along each tube 15 for selectively covering and uncovering openings 20. As the openings 20 are uncovered by slide 19, the sound volume to the listener decreases. Headset 16 is mounted on each tube 15 and comprises earpieces 17 in a manner similar to that which is shown in the solid-body embodiment at FIG. 4.

What is claimed is:

1. In combination with a stringed instrument having a bridge and a string anchor, apparatus for transmitting acoustical energy to a listener comprising a flexible energy pick-up chamber having at least one opening, said chamber being located in said bridge, so that one wall of said chamber provides support for the strings and there being substantially no soft, sound damping material between said wall and the strings; at least one elongated, hollow energy transmission member having a first end connected to the interior of said chamber through said opening; and listening means for transmitting said energy to a listener, said means being mounted on a second end of said hollow member.

2. Apparatus according to claim 1 wherein the hollow energy transmission member is a flexible tube.

3. Apparatus according to claim 2 wherein said chamber has two openings and an energy transmission member is connected to the interior of said chamber through each of said openings.

4. Apparatus according to claim 1 further comprising air flow control means to control the amount of acoustical energy being transmitted to said listener.

5. Apparatus according to claim 2 further comprising air flow control means wherein said means comprises adjustable compression means mounted on said energy transmission member for selectably changing the cross-sectional area of said member.

6. Apparatus according to claim 4 wherein said air flow control means comprises openings in said apparatus downstream of said chamber and means for selectably closing said openings.

7. Apparatus according to claim 3 wherein said listening means is a headset means comprising a pair of padded, concave earpieces surrounding each ear, each said earpiece having an opening therein, and the interior of each said earpiece being connected to one of said flexible tubes through said opening.

8. Apparatus according to claim 1 further comprising a chamber support to prevent the closing of said pick-up chamber by the pressure exerted by said strings.

9. Apparatus according to claim 8 wherein said pick-up chamber is tubular.

10. Apparatus according to claim 9 wherein said chamber support comprises a flexible C-shaped member encompassing said chamber on three sides and an anti-collapse member adjacent the fourth side of said chamber in the mouth of said C-shaped member to support said C-shaped member against the pressure exerted by said strings.

11. Apparatus according to claim 10 further comprising at least one string support mounted on said C-shaped member above said pick-up chamber to support said strings.

12. Apparatus according to claim 11 wherein said instrument has a plurality of strings;

each string is supported by a separate string support;

each string support is adjacent at least one other string support; and each said string support is mounted on a separate finger of said C-shaped member such that each string support is substantially resonantly isolated from each other string support.

13. Apparatus according to claim 12 wherein each string support is tubular and is tied to said finger by a durable string; and further comprising a clamping plate over each said string between said string supports and said string anchor to pressure each said string against each string support and promote resonant contact therebetween.

14. Apparatus in accordance with claim 9 wherein said chamber is constructed of a plastic material.

15. Apparatus according to claim 8 wherein said instrument has a substantially solid body.

16. Apparatus according to claim 8 wherein said instrument has an open-frame body.

17. Apparatus according to claim 15 wherein said bridge further comprises a damping material mounted on said instrument body below said chamber for minimizing the flow of acoustical energy from said strings through said bridge to said solid body.

18. Apparatus according to claim 1 wherein said bridge is mounted on adjusting means for moving said strings a selected distance from the body of said instrument.

19. Apparatus according to claim 8 further comprising a protective plate mounted above and covering said bridge to protect it from the hand of the player.

20. Apparatus according to claim 2 further comprising a tube support means located in bent portions of said flexible tube to prevent collapse thereof.

21. Apparatus according to claim 20 wherein said tube support means comprises a rigid tube.

22. Apparatus according to claim 8 wherein said chamber support comprises a chamber support means inside said chamber.

23. Apparatus according to claim 8 wherein said chamber support comprises a chamber support means located between said chamber and said string anchor.

* * * * *